(12) United States Patent
Inglis (10) Patent No.: US 7,640,256 B2
(45) Date of Patent: Dec. 29, 2009

(54) DATA COLLECTION CATALOGUING AND SEARCHING METHOD AND SYSTEM

(75) Inventor: Stuart John Inglis, Hamilton (NZ)

(73) Assignee: Real Time Genomics Inc., San Francisco, CA (US)

( * ) Notice: Subject to any disclaimer, the term of this patent is extended or adjusted under 35 U.S.C. 154(b) by 0 days.

(21) Appl. No.: 11/630,155

(22) PCT Filed: Jun. 17, 2005

(86) PCT No.: PCT/NZ2005/000134

§ 371 (c)(1),
(2), (4) Date: Mar. 25, 2008

(87) PCT Pub. No.: WO2005/124596

PCT Pub. Date: Dec. 29, 2005

(65) Prior Publication Data

US 2008/0256070 A1 Oct. 16, 2008

Related U.S. Application Data

(60) Provisional application No. 60/581,156, filed on Jun. 18, 2004.

(51) Int. Cl.
  *G06F 7/00* (2006.01)
  *G06F 17/00* (2006.01)
(52) U.S. Cl. .................... 707/100; 707/102; 707/104.1
(58) Field of Classification Search .................... 707/3, 707/5–7, 100–102, 200, 205, 104.1; 435/6
  See application file for complete search history.

(56) References Cited

U.S. PATENT DOCUMENTS

| | | | |
|---|---|---|---|
| 5,742,807 A | | 4/1998 | Masinter |
| 5,966,712 A | * | 10/1999 | Sabatini et al. .......... 707/104.1 |
| 6,023,659 A | * | 2/2000 | Seilhamer et al. ............. 702/19 |
| 6,773,886 B2 | * | 8/2004 | Kaufman et al. ................ 435/6 |
| 2002/0106649 A1 | * | 8/2002 | Lizardi et al. .................. 435/6 |
| 2004/0126770 A1 | * | 7/2004 | Kumar et al. .................. 435/6 |
| 2006/0057608 A1 | * | 3/2006 | Kaufman ........................ 435/6 |
| 2007/0088769 A1 | * | 4/2007 | Pace et al. .................. 707/204 |

FOREIGN PATENT DOCUMENTS

WO    WO 01/13268 A2    2/2001
WO    WO 2004/013769 A2    2/2004

OTHER PUBLICATIONS

Hugh E. Williams et al., Indexing and Retrieval for Genomic Databases, IEEE Transactions On Knowledge And Data Engineering, vol. 14, No. 1, Jan./Feb. 2002.
W.J. Wilbur et al., Rapid Similarity Searches of Nucleic Acid and Protein Data Banks, Proc. National Academy of Sciences, vol. 80, pp. 726-730, Feb. 1983.
D. Archambaud et al., Rapid-2, an Object-Oriented Associative Memory Applicable to Genome Data Processing, Proc. 27th Annual Hawaii International Conference on System Sciences, pp. 150-159, Jan. 1994.

(Continued)

*Primary Examiner*—Don Wong
*Assistant Examiner*—Merilyn P Nguyen
(74) *Attorney, Agent, or Firm*—Blakely, Sokoloff, Taylor & Zafman LLP (57) ABSTRACT

A method of cataloguing a data structure employs the formation of a catalogue data structure which is used to associate data items transformed from data elements present within the data collection with storage addresses of the original transformed data elements. This catalogue data structure may be sorted to facilitate searching through same to detect the presence of search patterns. Such searches may be completed through the formation of a plurality of search queries from a received search pattern sequence where the results of running these search queries may then be subsequently considered in conjunction with a search pattern sequence detection process.

25 Claims, 3 Drawing Sheets

OTHER PUBLICATIONS

A. Califano et al., FLASH: A Fast Look-Up Algorithm for String Homology, Proc. 1$^{st}$ International Conference on Intelligent Systems for Molecular Biology, pp. 56-64, 1993.

International Search Report for PCT/NZ2005/000134, mailed Oct. 13, 2005, 3 pages.

* cited by examiner

| 19 | 32 | 45 | 56 |
|----|----|----|----|
| 15 | 0  | 10 | 5  |

FIGURE 3

| G | T | C | A | G | T | C | G | A | G | T | C | A | A | C | G | T | A | G | A |
|---|---|---|---|---|---|---|---|---|---|---|---|---|---|---|---|---|---|---|---|
| G | T | C | A | G |   |   |   |   |   |   |   |   |   |   |   |   |   |   |   |
|   | T | C | A | G | T |   |   |   |   |   |   |   |   |   |   |   |   |   |   |
|   |   | C | A | G | T | C |   |   |   |   |   |   |   |   |   |   |   |   |   |
|   |   |   | A | G | T | C | G |   |   |   |   |   |   |   |   |   |   |   |   |
|   |   |   |   | G | T | C | G | A |   |   |   |   |   |   |   |   |   |   |   |
|   |   |   |   |   | T | C | G | A | G |   |   |   |   |   |   |   |   |   |   |
|   |   |   |   |   |   | C | G | A | G | T | . | . | . | . |   |   |   |   |   |

DATA COLLECTION CATALOGUING AND SEARCHING METHOD AND SYSTEM

CROSS-REFERENCE TO OTHER APPLICATIONS

This is a National Phase of International Application No. PCT/NZ2005/000134, filed on Jun. 17, 2005, which claims priority from U.S. Provisional Patent Application No. 60/581,156, filed on Jun. 18, 2004.

TECHNICAL FIELD

The present invention relates to systems and methods for indexing and searching patterns. In particular, the present invention introduces a packed data structure as an index useful in searching patterns. The present invention is particularly useful for searching large patterns, although other sizes of patterns may be searched.

BACKGROUND ART

In many fields, large amounts of pattern data have been accumulated and stored in innumerable databases. However, there is a lack of the capacity to utilize the enormous amounts of data collected and stored. There is mounting interest in compact and efficient database searching techniques to locate a variety of different patterns. Such patterns may include nucleotide sequences, amino acid (e.g. peptide) sequences, geological samples, binary data, textual data, etc. In the particular field of bioinformatics, attempts are made to understand the information stored in nucleotide sequences comprising DNA (and other nucleotide sequences) and their translation into molecules of life, as well as efforts to understand peptide sequences. In numerous applications in bioinformatics, it may be desirable to search for particular sequences of nucleotides and amino acids. Text pattern matching presents a major computational challenge because sequence databases are growing exponentially.

At times, genomes from different species are compared and analyzed by using techniques referred to as "comparative genomics". Researchers examine different features when comparing genomes: sequence similarity, gene location, the length and number of coding regions (called exons) within genes, the amount of noncoding DNA in each genome, and highly conserved regions maintained in organisms as simple as bacteria and as complex as humans. Comparative genomics involves the use of computer programs that can line up multiple genomes and look for regions of similarity among them. Tools, such as BLAST (available through NCBI), are available to perform such similarity searches.

As sequence data is generated, public databases are routinely scanned for similar sequences. Thereafter, sequence fragments may be collected by performing a cluster search to build into a larger consensus. Building consensus sequences and whole genomes requires pattern searches to find and mask repeat regions, followed by clustering searches and layered meta-clustering searches. In addition, comparative genomics requires large numbers of searches of different genomes to find related molecules. Given the current volume of sequence data and the speed at which it is growing, sequence searching is often a rate limiting step for modern genomics.

Most current searching methods look up pattern position information in a single array data structure. The index of this single array is often calculated by a function that maps the search pattern into a numeric index. The array is then examined at the location represented by the index. The array usually contains a reference to the positions of the patterns that are being searched. For example, the SSAHA (Sequence Search and Alignment by Hashing Algorithm, available through The Sanger Institute, Cambridge, UK) method stores a single array for all possible sequence indexes. For large pattern lengths, the single array methods will generate a large and often extremely sparse array.

For large patterns the size or length of this single array data structure can become substantial. This single array will need to provide an entry or storage position for each possible unique pattern which may be searched for, but which may not necessarily be present within the database to be indexed.

This scheme allows a rapid search to be completed for any particular pattern but can be impractical for large pattern sizes. A large number of unique combinations of symbols are available to make up long length patterns which in turn place significant demands on the memory of a computer system used to facilitate such methods. Furthermore, the single large indexing array employed in prior art methods is comparatively sparsely populated with data, again resulting in a relatively inefficient use of resources. As can be appreciated by those skilled in the art the memory resources used to implement such systems will increase exponentially with a linear increase in the length of the pattern searched for.

There is a need for a process that finds patterns faster than existing processes and that places no limits on word sizes. The search capability should be efficient and compact to decrease memory usage compared to memory requirements by current search techniques.

All references, including any patents or patent applications cited in this specification are hereby incorporated by reference. No admission is made that any reference constitutes prior art. The discussion of the references states what their authors assert, and the applicants reserve the right to challenge the accuracy and pertinency of the cited documents. It will be clearly understood that, although a number of prior art publications are referred to herein, this reference does not constitute an admission that any of these documents form part of the common general knowledge in the art, in New Zealand or in any other country.

It is acknowledged that the term 'comprise' may, under varying jurisdictions, be attributed with either an exclusive or an inclusive meaning. For the purpose of this specification, and unless otherwise noted, the term 'comprise' shall have an inclusive meaning—i.e. that it will be taken to mean an inclusion of not only the listed components it directly references, but also other non-specified components or elements. This rationale will also be used when the term 'comprised' or 'comprising' is used in relation to one or more steps in a method or process.

It is an object of the present invention to address the foregoing problems or at least to provide the public with a useful choice.

Further aspects and advantages of the present invention will become apparent from the ensuing description which is given by way of example only.

DISCLOSURE OF INVENTION

According to one aspect of the present invention there is provided a method of cataloguing a data collection composed of a plurality of data symbols, said data symbols having a defined order with respect to one another within the data collection, said method of cataloguing being characterised by the steps of;

(i) forming a first data element from an initial sequence of symbols present within the data collection, said data element being stored at a storage location within the data collection having a storage address, and
(ii) transforming the first data element into a first data item, said data item being capable of being ranked with respect to other data items, and
(iii) storing the first data item using an ordered catalogue data structure which defines a plurality of sequentially arranged storage positions, and
(iv) associating with the first data item the storage address from which the first data element was retrieved, and
(v) repeating steps (i) through (iv) for each data element required from the data collection, and
(vi) sorting the ordered catalogue data structure by ranking the data item stored within said catalogue data structure.

According to a further aspect of the present invention there is provided a method of cataloguing a data collection substantially as described above, further characterised by the additional subsequent steps of;
(vii) forming at least one ordered content data structure which defines a number of storage positions equal to or less than the maximum number of unique data elements which can exist, and
(viii) associating with each storage position at least one data element, and
(ix) storing within each storage position of the content data structure a positive or negative indicator depending on whether said at least one data element associated with the storage position is present within the data collection.

The present invention is adapted to provide a method, system and apparatus for cataloguing a data collection. The system or apparatus provided may include at least one computer system adapted to read a set of computer executable instructions recorded on computer readable media. These instructions, once executed by the computer system, may be adapted to perform the method of cataloguing discussed below. Furthermore, the data collection to be catalogued may also be provided in an electronic form, thereby allowing a computer system to read and catalogue the data it contains.

Preferably a catalogue produced in accordance with the present invention may consist of one or more ordered data structures which may in turn be searched to find particular data or patterns within the data present in the catalogued data collection.

In a preferred embodiment the data collection to be catalogued may be stored within an electronic database. Database technology is well known in the art and may be readily harnessed to store and retrieve large volumes of data or information.

Preferably the data collection to be catalogued may be composed of a large number of data symbols which have a defined order with respect to one another within the data collection. In a further preferred embodiment, the data symbols stored may be nucleotide sequences drawn from the four base pair symbols A, T, C and G. The sequence at which these symbols appear and also the sequence at which chunks or collections of these symbols are arranged with respect to one another is highly relevant. However, those skilled in the art should appreciate that other types of data elements, such as for example, peptide sequences, geological sample data, text based data or any other form of data which may be represented in a binary form may be held within a data collection to be catalogued in conjunction with the present invention.

In the preferred embodiment data elements may be formed from the stored symbols of the data collection using a sliding window process. The size of the window used may reflect the size of the resulting data element provided and a sliding displacement value associated with the window may determine the number of data elements which are generated from the symbols of the data collection. In these instances an initial data element may be formed by the initial number of symbols present within the data collection equal to the length of the window or the data element to be formed. To form the second data element this window may then be moved along a number of symbols equal to the displacement value associated with the window, with this displacement value being equal to one symbol at a minimum or equal to the length or size of the window at a maximum.

Those skilled in the art will appreciate that the displacement value associated with the sliding window technique used will determine the number of data elements generated or formed from the data collection. If the displacement value associated with this sliding window process is set to the standard length provided for data elements the resulting catalogue or data structure will have a size substantially equivalent to the size of the data collection catalogued. Conversely, larger catalogue data structures may be provided with smaller displacement values to give a higher resolution to search results obtained using such a catalogue data structure, at the expense of the memory used resources.

Preferably, a data element may be defined as a sequence of base pair symbols where the length of the sequence or number of symbols integrated into each element is determined by the performance required of the catalogue to be provided. As discussed further below, as the size of the data elements handled increases, the memory resource requirements of the present invention are reduced. Conversely, smaller data elements may be handled to give the system a higher search resolution, at the expense of requiring further memory resources to provide the catalogue required.

For the sake of expediency reference throughout this specification will be made to a single data element being formed from five base pair symbols of a nucleotide sequence. However, those skilled in the art should appreciate that different types of data elements of differing length or size may also be employed and reference to this particular selection should in no way be seen as limiting.

Reference throughout this specification will also be made to data elements and/or data items being formed from a number of symbols depending on the format of the item or element involved. Those skilled in the art should appreciate that these symbols may incorporate binary or any other base numeric symbols, other forms of alpha numeric symbols or any other form or representation of information. Furthermore, the order or precedence or arrangement of such symbols may also change the information contained within a data element or item where the sequence of symbols presented may include one or more most significant symbols which can give meaning, importance, rank or priority to the data element or item.

Single data elements may be stored at known locations or positions within the data collection. These known locations may be a memory address in RAM or on disc, or alternatively may consist of a base address with an added offset indicating the position at which the data involved is stored. Each of these locations or positions may therefore have a corresponding address which can be used to retrieve the data element involved.

Preferably each and every data element of the collection is subjected to a transform operation which produces a data item from a data element. The data items produced may have a format which allows them to be ranked or prioritised with respect to one another. In a further preferred embodiment, the transform applied to data elements may be similar to a hash function used in information technology data indexing applications which will result in a numeric format data item being generated. Numeric format data items may therefore be easily ranked or prioritised with respect to one another in a descending or ascending order.

In preferred embodiments the transform applied to data elements may be a direct hash function. Direct hash functions allow for provision of data items which encapsulate all the information present within data elements.

In some instances the size or length of the data element to be transformed may result in a data index which is larger than that which can be accommodated by the memory resources in computer hardware available. In such instances "lossy hashing" transform operations may be employed, which can result in the same data item being produced for two unique data elements. In such instances well known rehashing techniques may be employed to provide an alternative data item from the second data element. However, such rehashing techniques generally increase the computational overhead of the resulting cataloguing process, and any subsequent search process may need to complete multiple transforms on the data element searched for before being able to find the current data item within the catalogue data structure.

In some embodiments where lossy hashing transforms are used, a retrieval validation process may be implemented during a retrieval or search process. As each stored data item is associated with the storage address of the data element used to generate the data item, the original data element may be retrieved to validate whether the correct data item has been identified. If inconsistencies are present between the data element searched for and the data element retrieved, a subsequent rehashing or further transform operation may then be completed on the data element searched for to look for the alternative data item assigned to avoid a hash collision.

Preferably the present invention may also use an ordered catalogue data structure which defines a plurality of sequentially arranged storage positions. The data items discussed above may preferably be loaded and stored within the storage positions provided by the catalogue data structure, preferably with a sequential ordered arrangement. In a further preferred embodiment, an ordered catalogue data structure may be formed by an array. Arrays provide ordered linear data structures consisting of a single sequence of storage positions.

However in an alternative embodiment, for a large number of duplicate data items relating to the same data element to be stored, the catalogue data structure may store a flag or reference to a further duplicate based data structure. This duplicate based data structure may in turn be used to associate the data item with the plurality of storage addresses of each duplicate data element. In a further preferred embodiment such a duplicate based data structure may hold both the single data item value involved in addition to an array of storage addresses. In these instances the catalogue data structure may be effectively used to store data items through providing a flag or reference to the location of the further duplicate based data structure, as opposed to the data catalogue structure being used to directly store data items.

This aspect of the present invention may be employed to reduce the consumption of memory resources required to catalogue and subsequently search a data collection. Where a binary search or an interpolative search are employed on the catalogue data structure, a number of redundant search steps can normally be completed stepping through the same value of data item for duplicate data elements. By removing duplicate data items from being stored directly within the catalogue data structure such redundant search steps may be eliminated, therefore speeding the resulting search process.

Reference throughout this specification will also be made to the catalogue data structure employed being an array, but those skilled in the art should appreciate that other types of ordered data structures may also be used and reference to the above only throughout this specification should in no way be seen as limiting.

Preferably the size, length or number of storage positions of the catalogue data structure may be substantially equivalent to the number of data elements within the data collection when a sliding window displacement value equal to the length of the these data elements is provided. In such instances the size of the catalogue data structure may be said to be substantially equivalent to the size of the data collection. In such embodiments, the catalogue data structure may provide a packed, highly utilised structure which can optimise the use of memory resources required in conjunction with the present invention. Preferably, each resulting data item created may be sequentially loaded into the catalogue data structure in the order at which the data items are generated. Again however, those skilled in the art should appreciate that the catalogue data structure may initially be loaded with data items in any particular order or sequence required.

Furthermore, those skilled in the art should also appreciate that the size, length or number of storage positions of the catalogue data structure may not necessarily be equivalent to the size of the data collection where a sliding window data element generation process is used with window displacement value less than the fixed length of the data elements to be provided. In such embodiments a larger catalogue data structure may be provided to in turn give a higher resolution to the results of search is completed.

Preferably each and every data item may be associated with the storage address of the data element used to generate the data item. Such association of data items to storage addresses may cross reference these two types of information with respect to one another.

In a preferred embodiment, data items may be associated with storage addresses through the provision of an additional parallel address data structure. This address data structure may be substantially identical to the catalogue data structure in such embodiments and may align associated data items with storage addresses in a complimentary manner to provide the parallel characteristic required. In such embodiments any subsequent sorting, transformation or modification process completed on the catalogue data structure will in turn be completed on the address data structure to maintain the parallel association between data items and storage addresses required.

In a further preferred embodiment the parallel address data structure discussed above may be formed by an array. In instances where an array is used to provide the catalogue data structure an array can also be provided to implement the parallel characteristics of the address data structure required.

Reference throughout this specification will also be made to the present invention employing a paired parallel set of arrays to associate data items with storage locations. However, those skilled in the art should appreciate that alternative data structure implementations may be employed to achieve the same aims required. For example, in accordance with one alternative embodiment, the catalogue data structure may be expanded or also include storage positions for storage addresses to maintain an association with related data items.

Preferably, once the catalogue data structure has been filled with all available data items, these data items may be sorted into new positions depending on the rank or priority of each data item. For example, in one preferred embodiment, the lowest ranked data item may be placed at the first storage position, and the highest ranked data item placed at the last storage position of the catalogue data structure. Alternatively, a descending rank sort may be applied in other embodiments if required.

The sort operation executed with respect to the catalogue data structure may also be executed with respect to any parallel address data structure employed. By applying the same sort operation to the address data structure this will maintain the association between specific data items and cross referenced storage addresses.

Completing a sort operation on the data items allows relatively fast find operations to be completed on the catalogue data structure. For example, if a search is to be completed for a data item with a median rank value then an initial investigation can be made for the presence of this data item at positions near to the middle of the catalogue data structure.

In a further preferred embodiment the most significant symbol, bit or component of a data item may not be stored within the resulting sorted catalogue data structure discussed above. The most significant symbol, bit or component may be removed once this data structure is sorted, as this symbol or component will be common to all data items within a particular region of the data structure and therefore is not applicable to differentiating between different data items. For example, in a preferred embodiment where a numeric form data item is provided, the most significant digit of the numeric data item may not be stored to reduce the memory requirements of the present invention.

In a preferred embodiment a further ordered class data structure may also be employed in connection with the present invention. A class data structure may be implemented to provide pointers or references to sections of the catalogue data structure where these sections contain data items with a similar rank.

In a further preferred embodiment such a class data structure may define a set of storage positions which are to hold pointers to various sections or positions within the catalogue data structure which in turn hold data items with differences in their most significant symbol or component. Pointers may be made to the first instance of a difference in these most significant symbols to classify general regions or sections of the catalogue data structure as relating to data items with incremental rank differences. For example, in embodiments where a numeric format data item is used, a category data structure may be maintained which holds pointers to the sections of the catalogue data structure at which there is a change in the most significant digit of the data items stored.

In a further preferred embodiment a class data structure may be formed by an array where this array defines a number of storage positions equal to the number of most significant unique symbols used to rank data items. For example, if data items with numeric values ranging from 1 through 10,000 are provided, a class data structure may be implemented with pointers to sections of the category data structure which can be hundreds based, thousand based, two thousand based and so forth.

In a further preferred embodiment at least one content data structure may also be employed in conjunction with the present invention. A content data structure may be provided to give an overview of the current data elements held in the data collection to be catalogued, as opposed to the catalogue data structure employed to retrieve storage addresses.

Such an ordered content data structure may define a number of storage positions equal or less than to the maximum number of unique data elements which can exist. As can be appreciated by those skilled in the art this content data structure could be comparatively large, and potentially will grow in size as the default or set size of each data element increases. The maximum length or size of the content data structure will therefore be determined by the maximum number of unique data elements which could be contained within the data collection involved.

Preferably there may be associated with each storage position of the content data structure at least one data element. In a further preferred embodiment a lossy hash function may be used to associate a plurality of unique data elements with a single storage position of the content data structure. In such embodiments a relatively small, compact content data structure may be provided which has storage positions associated with every single unique data element which may be formed from the data symbols involved.

Preferably the content data structure may have stored within each of its storage positions a positive or negative indicator depending on whether at least one data element associated with the storage position is actually present within the data collection. These positive or negative indicators may consist of single bit encodings in some embodiments through to boolean objects or integer values in others, depending on the software and hardware platform used to implement the present invention. However it should be appreciated that the format of such indicators can be chosen to minimise the number of bytes required to implement the fully loaded content data structure involved.

Preferably a content data structure may be implemented through a single array similar to that discussed above with respect to the catalogue and address data structure. A single array can be readily formed and loaded with appropriate indicators to provide the content data structure required.

Preferably a content data structure may be used to quickly determine whether a particular data element is present within the data collection on inspection of the storage position associated with that data element. The presence of a positive or negative indicator at such a storage position can therefore be used to quickly ascertain whether the data element involved is present within the data collection. Furthermore in embodiments where a lossy hash function is used to associate plurality of data elements with a single storage position of the content data structure this quick check will indicate that at least one of the data elements associated with the storage position are present within the data collection.

This technique may also be applied to speed up searches completed on the basic catalogue data structure. An initial check may be made of the content data structure to determine whether a specific data element is present, and if so a search operation can then be completed on the catalogue data structure to find the address associated with the data element of interest. If the data element is not present this search process can terminate early.

In a further preferred embodiment a plurality of content data structures may be provided in accordance with the present invention. Each separate individual content data structure may employ a separate lossy hash function to map a plurality of unique data elements to a single storage position of the content data structure. As different lossy hash functions are employed across each of the content data structures, a check for the presence of a particular data element across all content data structures can reduce uncertainty as to whether that particular data element is present within the data collection catalogued.

According to a further aspect of the present invention there is provided a method of detecting the presence of search patterns within a data collection catalogued substantially as described above, said method being characterised by the steps of;

i) receiving a search pattern sequence, and
ii) forming a plurality of search queries by running a sliding window process over the received search pattern sequence, and
iii) retrieving a plurality of storage addresses from the catalogue data structure, said search addresses being associated with data elements which match the search queries formed, and
iv) detecting the presence of the search pattern sequence received by inspecting the spatial relationship between the storage addresses received.

The present invention may provide efficient techniques for database storage and searching of a variety of different types of patterns. The pattern may comprise a nucleotide sequence, peptide sequence, geological sample, binary data, textual data, and so forth.

Preferably the pattern or data element symbol sequences to be searched may exceed the size of the data element used to catalogue the data collection involved. In general terms search patterns may consist of sequences of data element symbols with a length greater than that normally found in two or more data elements.

In preferred embodiments a plurality of search queries may be run to find a single data sequence pattern in conjunction with the present invention.

In such embodiments the data sequence to be searched for may be broken down into sets of symbols with a length equal to the length of a standard data element. A number of queries for various data elements may be formed using a sliding window process with this window being moved sequentially along the search pattern a fixed displacement of data symbols, ranging from one through to the number of data symbols usually present within a data element. In such embodiments an initial search query may be formed by the first data element present within the sequence to be searched. The next search query may be taken from the search sequence at a point displaced from the start of the sequence by the displacement value fixed for the sliding window. At this point a further data element size search query may be generated, and then the windows slid on through the search sequence again by the window displacement value and a further data element sized query can be extracted. This process will then continue until the last full length data element sized search query is extracted from the search sequence provided.

Those skilled in the art should appreciate that this sliding window approach will generate a large number of search queries for small window displacement sizes and a minimum number of queries when the window's displacement value is equal to the length of the data element employed. The size of the sliding window may preferably be controlled by the user depending on the memory resources available which the present invention may use. By using a small window displacement at each step a more comprehensive set of search queries will be generated resulting in a comparatively large number of search results.

The present invention may also implement a search pattern sequence detection process. This process may be used when a number of search queries have been run using the catalogue data structure to generate a series of hits composed of data elements with associated storage addresses.

In a preferred embodiment the detection of a pattern from the search results may be made through an inspection of the spacial relationship between the storage address retrieved for specific sequences of data elements. For example, in some instances a search pattern may be detected if a sequence of data elements are found which match the original search sequence and where these data elements are stored adjacent and sequentially with respect to one another within the data collection, as indicated by the retrieved or associated storage addresses involved.

In a further preferred embodiment an error threshold may be built into such pattern or sequence detection processes through allowing a maximum number of inconsistent data element symbols within a sequence while still classifying the sequence as a pattern match. In such instances a threshold error level may be set by a user, allowing the maximum number of symbol inconsistencies for a particular length search sequence or pattern which will still allow a collection of search hits to be classified as a detected pattern.

The pattern location is preferably determined within the database by consuming relatively low storage space. The resource requirements are inversely proportional to the time allowed for the searching method to complete. In particular, the present invention provides for optimizing resource requirements for pattern matching by using a scaling and sampling technique that decreases as the word size of the pattern match increases. Through the provision of one or more highly utilised or packed data structures the present invention may allow the location of a particular pattern or data element to be readily found. Furthermore, as the size or length of the pattern or data element increases the resulting load place on memory resources used are decreased. Conversely, a higher resolution search may be completed for smaller length patterns within a data collection, at the expense of an increase in the memory resources required.

The method provided may also include selection of a sampling function that is dependent on resource requirements. Furthermore, the patterns are preferably stored in a set of parallel arrays in a manner that permits a search speed that is independent of the length of the arrays. The present techniques are scalable to extremely large data sets, e.g. genomic sequences. Additional computational resources may be provided to further increase the search speed, although the present method has been designed for searching capabilities over the resource spectrum.

The data structure created for pattern searching and storage preferably includes an array of index values paired with an array of sequence positional information. Optimized hash functions may be provided for indexing of large patterns with decreased hash function collision. At least portions of the data structure may reside in RAM, external storage mediums, e.g. disk, multiple CPU's, and/or multiple computer systems.

The patterns that are stored and searched according to the present invention may be useful in a wide variety of areas. For example, the patterns may form a component in a data encryption system. In another embodiment, the patterns may be used in a telecommunication system. Furthermore, the patterns may be analyzed as part of a clustering system. The patterns may also be used for function assignment, mutation searching, SNP scans, building consensi or whole genomes, and orthologue finding. In still other embodiments, the patterns are useful in database engines, image analysis or processing, sound analysis or processing, radio or deep space frequency analysis, and analysis of data or signals originating from the ocean or from space. At times, the patterns may find use in analysis of the human or animal body, molecular imaging, and chemical or spectral analysis.

This pattern search capability is particularly desirable for use in comparative genomics that typically requires massive investment in sequence comparison capabilities. The paired arrays of the present invention may be used for performing pattern comparison, e.g. for genomic assembly, data assembly, fragment assembly, finding repeated genomic regions ("repeats"), etc.

In one embodiment, other present or future search processes may be combined with the present method and system to enhance the overall performance. For example, the SSAHA method of genomic searching is improved by efficiently storing the genomic information in the packed data structure of parallel arrays according to the present method. The SSAHA algorithm creates a sparse structure of $4^k$ bins for the k-tuples. This structure provides a direct mapping from any nucleotide sub-sequence to their positions in the sequence. This invention records the position information efficiently and creates a dense structure of size (L/k) that decreases as k increases and enables extremely large values of k to be used.

BRIEF DESCRIPTION OF DRAWINGS

The present invention is illustrated by way of example in the figures of the accompanying drawings and the figures are not intended for limitation, which figures are not intended to limit the present invention, and in which.

BEST MODES FOR CARRYING OUT THE INVENTION

The present invention includes a pattern search capability, which employs a strategy for managing the search phase of pattern searches in a database. One aspect of the present method includes a compact representation of a pattern in a given database. The representation includes pattern information mapped to positional information. This efficient representation allows any specific pattern to be rapidly located.

The present method improves on previous single array techniques by employing multiple arrays, i.e. at least two arrays, comprising cross-reference data to track positional pattern information. The arrays are usually aligned in parallel to allow for easy cross-reference of associated data. However, other methods of alignments and methods of cross-referencing the data in the arrays may be employed.

A first array, herein referred to as "index[ ] array", is a packed representation of the data of the database. The first array consists of "index" values. A second array, herein referred to as "location[ ] array", points to the location of specific sub-patterns in the database and comprises pattern location information. The index values of the first array are paired with the location information of the second array.

To find any specific index, the index[ ] array must be searched to find the location of the specific index in the index array. If a match is found (i.e. the specific query exists) then the paired location[ ] array is examined to find the location of the pattern in the database. The compact approach of the present invention trades off decreased memory usage for a more complex searching strategy. The arrays are searched to locate the matching pattern, rather than simply looking up the index into the array.

To create the data structure, the index[ ] array is populated by dividing the database into non-overlapping chunks. Each chunk has a length of k. The chunks are each converted to an index value. The conversion from an input pattern into a numeric index is a process known as "indexing". The index can be calculated in several ways. The type of indexing strategy may vary depending upon, inter alla, the word size (k), alphabet size (a) and/or the type of pattern being searched, such as nucleotide or peptide sequences.

In general, if the template is small enough to fit into the word size of the CPU (usually 32 or 64 bits) then the chunk can be converted directly to an index by performing a base conversion. For example, for a pattern that consists of nucleotides, each nucleotide base may be converted using A=0, C=1, G=2, T=3. If the template is too large to fix into the word size, the chunk can be converted to an index using a hash function.

One embodiment of indexing may employ a direct mapping technique for assigning index values. In the specific case where a 64-bit integer represents the index values and a=4 size alphabet represents genetic nucleotides, it is possible to store a k=32 length pattern (allowing 2 bits or $2^2$=4 possibilities per character gives 64 bits/2 bits/character=32 characters) or k=12 peptide pattern (allowing 5 bits or $2^5$=32 possibilities per character gives 64 bits/5 bits/character=12 characters).

This translation process from a pattern to a numeric index is often referred to as "hashing". There is a distinction between direct mapping where the index can be stored either optimally or sub-optimally. A technique, referred to herein as "lossy hashing", is when precision is lost during the conversion of the pattern into the index. For the genomic illustration, the mapping is direct when k≦32 (a=4 for nucleotides) or k≦12 (a=20 for amino acids), or uses lossy hashing when k>32 (a=4) or k>12 (a=20).

The optional lossy hashing method is a complex function that consistently maps a pattern to a pseudo-random number. The key attribute that separates a hash function from direct mapping function is that the maximum value of the index is known in advance in hashing, whereas, for the direct calculation method the maximum value is potentially unbound. The hash index value will always be in a certain range. Furthermore, the nature of the hash functions means that sometimes two patterns may hash to the same index value, referred to as a "hash collision".

For each data chunk, the position in the database is stored in an associated location[ ] array. The location[ ] array is usually positioned in parallel to the index array and with its location data aligned with associated index value data of the index[ ] array. Hence, for a given specific position i in the index[ ] array, index[i] refers to the index value at position i in the array. In the corresponding location[ ] array, location[i] refers to the location information at position i.

Once the pair of arrays has been populated by processing the entire database, the index[ ] array data may be sorted, such as sorting by increasing numerical order. Such sorting may be particularly desirable for searching large patterns. Accordingly, the paired location[ ] array may be also sorted to maintain data in parallel relation with the data in the index[ ] array. The sorted index[ ] array may be used to quickly find whether any arbitrary index value exists in the index[ ] array.

During an index searching phase, a quick determination may be made as to whether any arbitrary "key" is present in the index[ ] array. A variety of efficient methods may be employed for quickly finding whether the key exists.

For large k values, it is often the case that no specific exact match is found. To optimize this common case, a bit vector array, herein referred to as "bitvector[ ]", may be constructed to quickly determined whether any specific index value is not in the index[ ]. The bitvector[ ] stores a single bit to represent whether a specific index value occurs anywhere in the index[ ] array. By initially checking the compact bitvector[ ], there is no need to search the entire index[ ] array when the key is not present in the database.

Furthermore, efficient search of the index[ ] array may include performing an interpolation search with an initial guess as to the position in the array. The initial guess is determined as a function of the key. This estimation of the most likely position of the key in the index[ ] array, is an improved approach to standard binary searches.

For any specific key, the result of the index searching stage may include that no index match is found, or that a set of indices is found coupled with the matching set of locations.

To find matches from input search pattern within a database that has been indexed using the present method, each pattern may be searched against the database. The search pattern may be broken into k overlapping chunks and converted into an array of search indices, herein referred to as "search[ ] array", which represent the search pattern. Each of the index entries in the search[ ] array is searched using the previously described method. Since each hit search can return a number of hits, a set of hit index values, herein referred to as "chunkhit[ ]", is generated. Each entry in this array is entry recording database position information.

The set of chunk hits may be collated by converting the set into a set array of hits[ ]. Each entry in the hits[ ] array is a reference to the location information, such as the position in the search pattern and/or position in the database, as well as the chunk frequency count.

Once the hits have been collected a number of filter operations may be performed to reduce the amount of results. Various filtering operations that may be performed include filtering specific hits (or chunk matches), as well as filtering entire pattern matches. Some examples of specific types of filtering include filtering specific hits if the frequency is too low; filtering specific hits if the frequency is too high; removing all hits if the maximum frequency of any matched chunk is too high; and removing all hits based on applying a threshold to a linear function of x*(maximum frequency)−y*|hits|.

After a search has been performed the results from the hit filtering stage are in the form of an array of hits, herein referred to as "hits[ ]". Optionally, a number of ranking techniques may be used on the results. Some such ranking techniques are based on the total number of chunk hits; the linear function in the filtering section above; and a delta gap function, which combines the total pattern match with the distance between the hit chunks.

The output search results may be summarized in several ways. For example, the output may include a list of matching patterns; a list of matching patterns and their scores ranked by their sorted score; a specific sub-pattern that has matched the search string; and/or a set of sub-patterns aligned using a third party tool (such as bl2seq).

EXAMPLE 1

Figure 1:
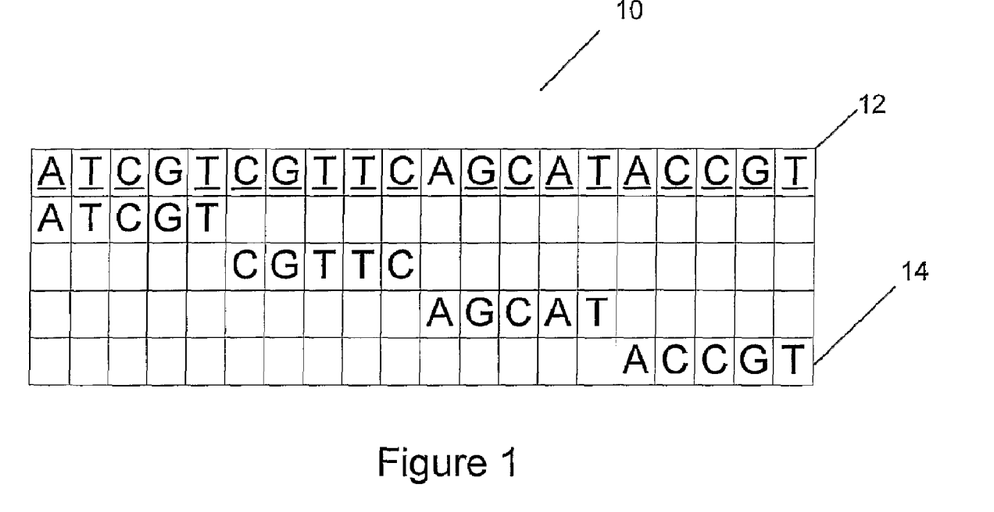
FIG. 1 is an illustration of one embodiment for partitioning an input pattern, in accordance with a preferred embodiment of the present invention.
Figure 2:
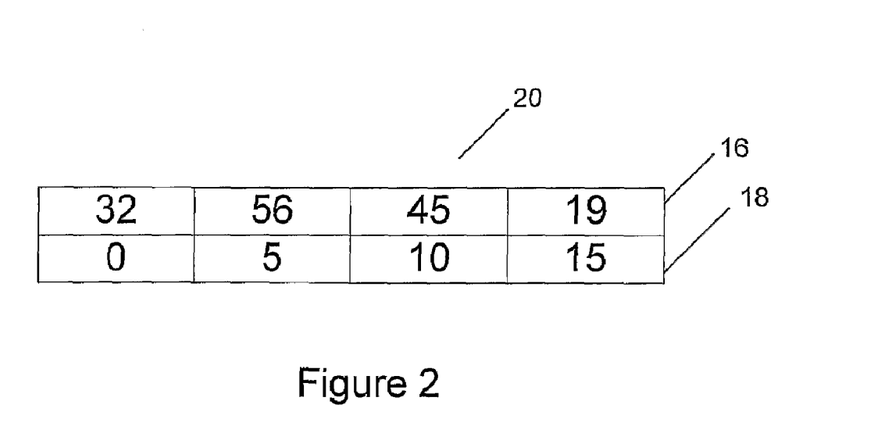
FIG. 2 is a block diagram of parallel arrays representing the input pattern of FIG. 1, in accordance with the present invention.

A search is performed on an original input pattern that is a nucleotide sequence comprising, "A T C G T C G T T C A G C A T A C C G T". As shown in an illustration (10) of FIG. 1, the input pattern (12) has a k=5 non-overlapping contiguous window applied across it. The input sequence pattern is broken into four data chunks (14), "ATCGT, CGTTC, AGCAT and ACCGT". Each of the four chunks is converted into a decimal index, e.g. 32, 56, 45 and 19 in an index[ ] array (16) of a parallel array table (20), as shown in FIG. 2. A location[ ] array (18) includes data representing the position of each data chunk in original file. In this example, the data chunk with the index 32 is at position 0, the chunk with index 56 is at position 5, the chunk with index 45 is at position 10, and the chunk with index 19 is at position 15.

To find the location of a particular data chunk, a chunk with the correct index is found and the corresponding position is cross-referenced. According to the parallel arrays table, if the first row is examined for the chunk having an index of 45, the chunk will be found at position 10 in the original file.

For a large pattern there will be (Length/k) columns in the parallel array table. For example, an array table for the human genome may have about 500,000,000 entries. When there are a large number of entries in the parallel array table, it is too time consuming to simply scan the array and look for a matching index. A more efficient search technique is required.

Figure 3:
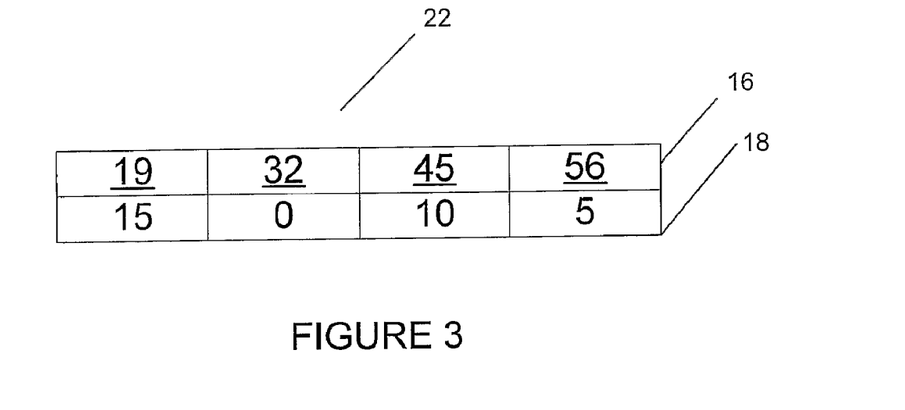
FIG. 3 is a block diagram of sorted arrays representing the parallel arrays of FIG. 2, in accordance with the present invention.

The first stage is to sort the parallel array table by the index. Originally, the table is often sorted by the position because position may be used for searching. However, in this case, sorting is desirable because the chunk index is used for the searching, rather than the position. The sorted arrays (22) for the present example are depicted in FIG. 3, comprising a sorted index[ ] array (16) and a sorted location[ ] array (18). For k=5, an array table (22) of 8 elements is required, which includes an array of 4 for the chunk indices and a parallel array of 4 for the positional information. If 8 bytes per element is used, then 64 bytes of storage is required.

By comparison, a single array technique usually requires much more storage capabilities. For example, SSAHA requires $4^{k+1}+8C$ bytes[1] where C is the number of chunks. This converts 4128 bytes to (4096+32). Thus, according to the present example, the SSAHA process requires 64 times more RAM than the storage requirement of the present invention to store the same structure as stored by the present invention. The savings realized by use of the present invention are impressive as k increases on real data.

[1] From the SSAHA: A Fast Search Method for Large DNA Databases, Genome Research, 2001

Figure 4:
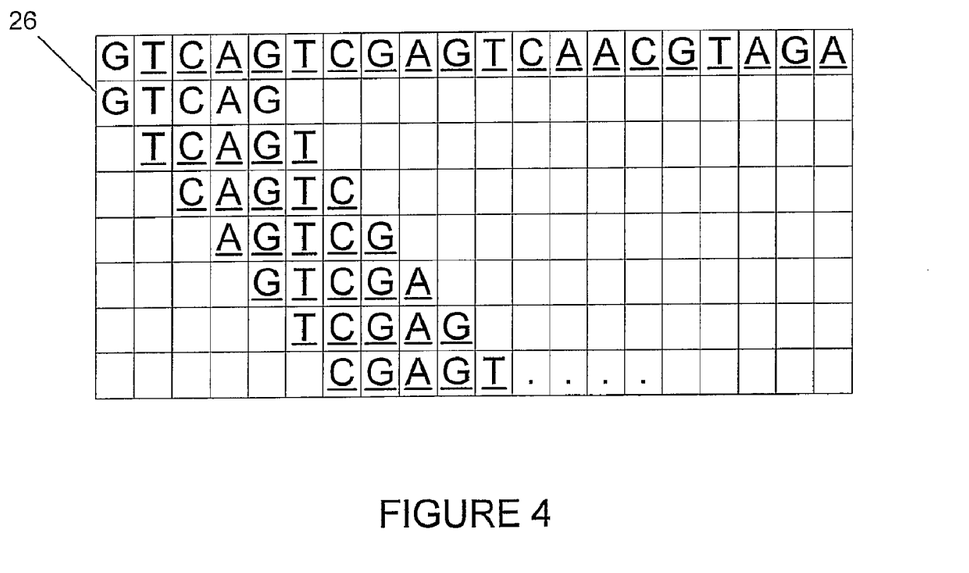
FIG. 4 is an illustration of one embodiment for searching the input pattern shown in FIG. 1, in accordance with the present invention.

FIG. 4 shows one embodiment of a method of searching. During searching the k=5 template (26) is slid over the search string. Each of the chunks is mapped to an index value.

There are a large number of efficient algorithms available for finding the index in the (index, position) array shown in FIG. 3. These methods include binary searching, which has complexity O(log L). In binary searching, a low/high bound is found and tested in the middle. If the value at the position is too low or high, the bounds are adjusted and the process is iterated.

EXAMPLE 2

Performance was assessed on large data sets compared to current search techniques. A genomic sequence comparison is made by using the present invention and using the current search baseline, BLAST. Each of the 5 million HTG reads of the *Populus balsamifera*, subspecies trichocarpa genome was compared with each other (effectively 25 million comparisons). The present method resulted in a comparison of all sequences 10,782 times faster than the search time of the BLAST method. The experiment was performed on an AMD Opteron 244 with two 64-bit 1.8 GHz processors and 12 GB of RAM running Linux. With the present invention, the bigger the job, the greater the differential with other current search methods.

Figure 5:
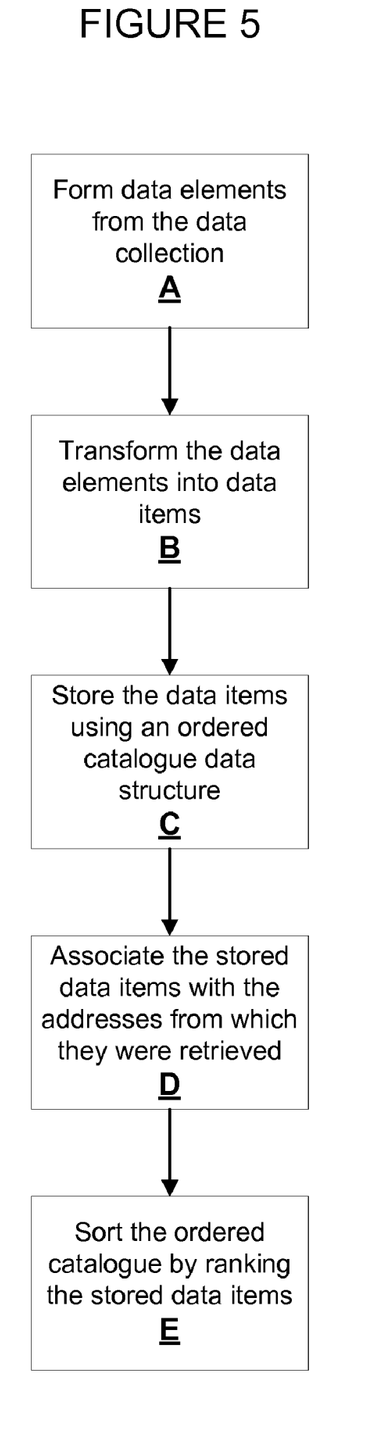
FIG. 5 shows a block schematic flowchart of a basic cataloguing processes executed in accordance with one embodiment of the present invention.

FIG. 5 shows a block schematic flowchart of a basic cataloguing process executed in accordance with one embodiment of the present invention. At the initial step A of this process the data collection to be catalogued is divided into a number of fixed length data elements.

The next step of this process B a transform function is applied to each element formed to result in a data item for each data element. Preferably this transform is implemented through a direct hash function.

At stage C each data item is stored within an ordered catalogue data structure, preferably formed by an array.

At stage D each stored data item is associated with the originating memory address of the data element which is used to form the data item. Preferably this step is completed by storing these addresses in a parallel address data structure.

In the last stage E of this process both the catalogue data structure and the associated parallel address data structure (provided in preferred embodiments) are sorted based on a rank indication provided by the form of each data item.

Figure 6:
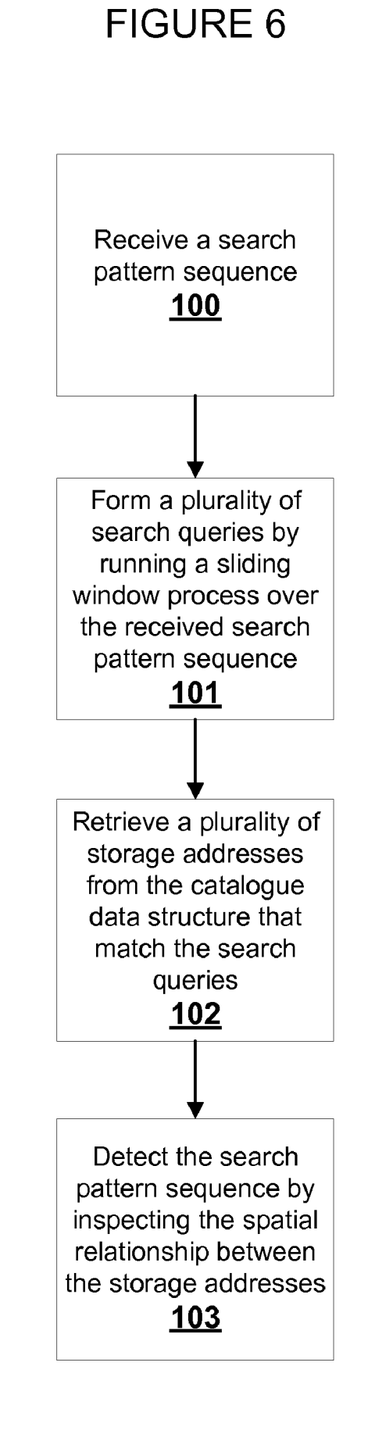
FIG. 6 illustrates a basic schematic flowchart of a basic search and pattern detection process provided in accordance with one embodiment of the present invention.

FIG. 6 illustrates a basic schematic flowchart of a search and pattern detection process provided in accordance with one embodiment of the present invention.

In the first stage 100 of this process, a search pattern sequence is received where the presence of this pattern is to be detected within a catalogued data collection.

At the next stage 101 a plurality of search queries are formed from the received search pattern by applying a sliding window process to the received search pattern. The number of search queries formed will depend on the displacement value assigned to this sliding window process.

At the next stage 102 a plurality of storage addresses are retrieved from the catalogue data structure provided, where each of the retrieved addresses are associated with data elements which match the search queries formed in stage 101.

At the last stage 103 a pattern sequence detection process is run over the retrieved storage addresses to detect a pattern through inspecting the spatial relationship between the retrieved storage addresses.

The present invention has been described above in varied detail by reference to particular embodiments and figures. However, these specifics should not be construed as limitations on the scope of the invention, but merely as illustrations of some of the present embodiments. It is to be further understood that other modifications or substitutions may be made to the described system, as well as methods of its use without departing from the broad scope of the invention.

Aspects of the present invention have been described by way of example only and it should be appreciated that modifications and additions may be made thereto without departing from the scope thereof as defined in the appended claims.

What is claimed:

1. A method of cataloguing a data collection composed of a plurality of data symbols, said data symbols having a defined order with respect to one another within the data collection, said method of cataloguing comprising:
   (i) forming a first data element from an initial sequencing of symbols present within the data collection, said first data element being stored at a storage location within the data collection having a storage address,
   (ii) transforming the first data element into a first data item, said first data item being capable of being ranked with respect to other data items,
   (iii) storing the first data item using an ordered catalogue data structure which defines a plurality of sequentially arranged storage positions,
   (iv) associating with the first data item the storage address from which the first data element was retrieved,
   (v) consecutively repeating steps (i) through (iv) for each adjacent data element from the data collection, where each subsequent adjacent data element is formed from the same number of symbols as that used to form the first data element, and
   (vi) sorting the ordered catalogue data structure by ranking the data items stored within said catalogue data structure.

2. The method of cataloguing a data collection as claimed in claim 1, wherein the size of the catalogue data structure is equivalent to the size of the data collection.

3. The method of cataloguing a data collection as claimed in claim 1, wherein the catalogue data structure is formed from an array.

4. The method of cataloguing a data collection as claimed in claim 1, wherein data items are associated with storage addresses through the provision of a parallel address data structure.

5. The method of cataloguing a data collection as claimed in claim 4 wherein the parallel address data structure is formed from an array.

6. The method of cataloguing a data collection as claimed in claim 1 wherein data items are associated with storage addresses through the provision of a duplicate based data structure.

7. The method of cataloguing a data collection as claimed in claim 1 wherein the transform process applied to data elements provides numeric format data elements.

8. The method of cataloguing a data collection as claimed in claim 1 wherein the transform process applied to data elements is implemented by a direct hash function.

9. The method of cataloguing a data collection as claimed in claim 1 wherein the transform process applied to data elements is implemented by a lossy hash function.

10. The method of cataloguing a data collection as claimed in claim 9 wherein a retrieval validation process is executed within a search process which uses the catalogue data structure.

11. The method of cataloguing a data collection as claimed in claim 1 wherein a most significant symbol of the data items is not stored within the sorted catalogue data structure.

12. The method of cataloguing a data collection as claimed in claim 1 wherein a class data structure is provided.

13. The method of cataloguing a data collection as claimed in claim 12 wherein a number of unique most significant signals are present within the data items and the class data structure is provided by an array which defines a number of storage positions equal to the number of unique most significant symbols present within data items.

14. The method of cataloguing a data collection as claimed in claim 1, further comprising;
   (vii) forming at least one ordered content data structure which defines a number of storage positions equal to a maximum number of unique data elements which can exist,
   (viii) associating with each storage position at least one data element, and
   (ix) storing within each storage position of the content data structure a positive or negative indicator depending on whether said at least one data element associated with the storage position is present within the data collection.

15. The method of cataloguing a data collection as claimed in claim 14 wherein the content data structure is formed from an array.

16. The method of cataloguing a data collection as claimed in claim 1 wherein the catalogue data structure is used to find specific data element symbol sequences by running a plurality of search queries generated from a data element symbol sequence.

17. The method of cataloguing a data collection as claimed in claim 16 wherein the plurality of search queries run are generated using a sliding window process.

18. The method of cataloguing a data collection as claimed in claim 17 wherein the results generated by the plurality of search queries run are processed by a search pattern sequence detection process.

19. The method of cataloguing a data collection as claimed in claim 18 wherein the search pattern sequence detection process detects the presence of a pattern on inspection of the spatial relationship between storage addresses associated with data elements found by said search queries.

20. The method of cataloguing a data collection as claimed in claim 19 wherein an error tolerance threshold is used to test whether matching pattern sequences have been detected.

21. The method of claim 1 further comprising:
   receiving a search pattern sequence,
   forming a plurality of search queries by running a sliding window process over the received search pattern sequence,
   retrieving a plurality of storage addresses from the catalogue data structure, said storage addresses being associated with data elements which match the search queries and having a spatial relationship, and
   detecting a presence of the search pattern sequence received by inspecting the spatial relationship between the storage addresses received.

22. The method as claimed in claim 21 wherein an error tolerant threshold is used to test whether matching pattern sequences have been detected.

23. The method of cataloguing a data collection as claimed in claim 13 wherein data items are associated with storage addresses throughout the storage of storage addresses within the content data structure.

24. Computer executable instructions stored on a computer readable storage medium, said computer executable instructions being adapted to execute the method of cataloguing a data collection composed of a plurality of data symbols, said data symbols having a defined order with respect to one another within the data collection, said method of cataloguing comprising:
   (i) forming a first data element from an initial sequencing of symbols present within the data collection, said first data element being stored at a storage location within the data collection having a storage address, and
   (ii) transforming the first data element into a first data item, said first data item being capable of being ranked with respect to other data items, and
   (iii) storing the first data item using an ordered catalogue data structure which defines a plurality of sequentially arranged storage positions, and
   (iv) associating with the first data item the storage address from which the first data element was retrieved, and
   (v) consecutively repeating steps (i) through (iv) for each adjacent data element from the data collection, where each subsequent adjacent data element is formed from the same number of symbols as that used to form the first data element, and
   (vi) sorting the ordered catalogue data structure by ranking the data items stored within said catalogue data structure.

25. A computer readable storage medium with computer executable instructions stored therein, said computer executable instructions being adapted to execute the method of cataloguing a data collection composed of a plurality of data symbols, said data symbols having a defined order with respect to one another within the data collection, said method of cataloguing comprising:
   (i) forming a first data element from an initial sequencing of symbols present within the data collection, said first data element being stored at a storage location within the data collection having a storage address, and
   (ii) transforming the first data element into a first data item, said first data item being capable of being ranked with respect to other data items, and
   (iii) storing the first data item using an ordered catalogue data structure which defines a plurality of sequentially arranged storage positions, and
   (iv) associating with the first data item the storage address from which the first data element was retrieved, and
   (v) consecutively repeating steps (i) through (iv) for each adjacent data element from the data collection, where each subsequent adjacent data element is formed from the same number of symbols as that used to form the first data element, and
   (vi) sorting the ordered catalogue data structure by ranking the data items stored within said catalogue data structure.

* * * * *